United States Patent [19]

McWilliams et al.

[11] Patent Number: 4,908,342

[45] Date of Patent: Mar. 13, 1990

[54] ZSM-5 ZEOLITES HAVING UNIFORMLY LARGE CRYSTALS

[75] Inventors: John P. McWilliams, Woodbury; Catherine T. Sigal, Pennington, both of N.J.

[73] Assignee: Mobil Oil Corporation, New York, N.Y.

[21] Appl. No.: 18,747

[22] Filed: Mar. 3, 1987

Related U.S. Application Data

[63] Continuation of Ser. No. 773,101, Sep. 4, 1985, abandoned, which is a continuation-in-part of Ser. No. 647,501, Sep. 5, 1984, abandoned.

[51] Int. Cl.$^4$ .............................................. B01J 29/28
[52] U.S. Cl. ...................................... 502/68; 502/64; 502/71
[58] Field of Search .............................. 502/71, 64, 68

[56] References Cited

U.S. PATENT DOCUMENTS

| | | | |
|---|---|---|---|
| 3,790,471 | 2/1974 | Argauer et al. | 502/71 |
| 3,849,463 | 11/1974 | Dwyer et al. | 260/448 |
| 3,941,871 | 3/1976 | Dwyer et al. | 423/326 |
| 3,976,598 | 8/1976 | Daviditz | 423/328 |
| 4,100,215 | 7/1978 | Chen | 260/671 |
| 4,182,923 | 1/1980 | Chu | 585/475 |
| 4,375,458 | 3/1983 | Dwyer et al. | 423/329 |

FOREIGN PATENT DOCUMENTS

| | | |
|---|---|---|
| 536561 | 6/1980 | Australia . |
| 536830 | 6/1980 | Australia . |
| 537988 | 6/1980 | Australia . |
| 0057016 | 8/1982 | European Pat. Off. ............ 423/329 |
| 0065400 | 11/1982 | European Pat. Off. ............ 423/328 |
| 0065401 | 11/1982 | European Pat. Off. ............ 423/328 |
| 3212106 | 6/1983 | Fed. Rep. of Germany ...... 423/328 |
| 0007817 | 1/1982 | Japan ................................... 423/328 |
| 1003266 | 9/1965 | United Kingdom ................. 502/60 |
| 1581513 | 12/1980 | United Kingdom . |
| 1601915 | 11/1981 | United Kingdom . |

OTHER PUBLICATIONS

Ryszard Mostowicz et al., "Morphological Study of ZSM-5 grown in the 12Na$_2$O14.5(TPA)$_2$O System", Zeolites, vol. 3, No. 3, Jul. 1983, pp. 219-225.

M. Ghamami and L. B. Sand, "Synthesis and Crystal Growth of Zeolite [NH$_4$, TPA]-ZSM-5", Zeolites 1983, vol. 3, pp. 155-162, Apr.

Primary Examiner—Carl F. Dees
Attorney, Agent, or Firm—A. J. McKillop; C. J. Speciale; Edward F. Kenehan, Jr.

[57] ABSTRACT

There is provided an improvement for making large crystallite ZSM-5 zeolites by a method comprising forming the zeolite in a medium containing a combination of tetramethylammonium and tetrapropylammonium cations. The improvement involves the addition of sodium chloride to the aqueous reaction medium to increase the uniformity of crystallite size and to increase the mean crystallite size. Also provided are catalysts comprising these ZSM-5 crystallites and processes for converting organic compounds with these catalysts.

7 Claims, No Drawings

ZSM-5 ZEOLITES HAVING UNIFORMLY LARGE CRYSTALS

This is a continuation of copending application Ser. No. 73,101, filed on Sept. 4, 1985 now abandoned, which is a continuation-in-part of copending application Ser. No. 647,501, filed on Sept. 5, 1984 (now abandoned).

BACKGROUND

This invention relates to ZSM-5 zeolites having uniformly large crystals, the synthesis thereof and the use thereof as catalysts in organic compound conversions.

Zeolitic materials, both natural and synthetic, have been known in the past to have catalytic capability for various types of hydrocarbon conversion reactions. Certain of these zeolitic materials comprising ordered porous crystalline aluminosilicates have a definite crystalline structure, as determined by X-ray diffraction, within which there are a number of small cavities which are interconnected by a number of still smaller channels. These cavities and channels are precisely uniform in size within a specific zeolitic material. Since the dimensions of these pores are such as to accept for adsorption purposes molecules of certain dimensions while rejecting those of larger dimension, these materials have commonly been known to be "molecular sieves" and are utilized in a variety of ways to take advantage of the adsorptive properties of these compositions.

Crystalline aluminosilicates have been characterized by the presence of aluminum and silicon, the total of such atoms to oxygen being 1:2. The amount of alumina present in conventional aluminosilicates appears directly related to acidity characteristics of the resulting product. Low alumina content is advantageous in attaining low acidity, desirable for low coking and low aging rates.

U.S. Pat. No. 3,941,871 discloses the preparation of zeolites such as ZSM-5 having a high $SiO_2$ to $Al_2O_3$ ratio. The disclosure of this patent includes a teaching of the combined use of tetrapropylammonium (TPA) ions and tetramethylammonium (TMA) ions to make a crystalline metal organosilicate. U.S. Pat. No. 3,849,463 discloses a method of decreasing silica occlusion in a zeolite having a $SiO_2/Al_2O_3$ ratio of greater than 6 by incorporating in the reaction mixture an alkali metal salt.

The Dwyer et al U.S. Pat. No. 4,375,458, the entire disclosure of which is expressly incorporated herein by reference, describes a method for making large crystallite zeolites. More particularly, this Dwyer et al patent describes a method for preparing a crystalline zeolite having a $SiO_2$ to $Al_2O_3$ molar ratio of from about 25 to 1000 and having a crystal size at least 1 micron, the method comprising having in the reaction mixture (1) a combination comprising two different alkylammonium cations or (2) a combination comprising an alkylammonium cation and a metallic cation, wherein in combination (1) at least one of the alkylammonium cations and in combination (2) at least the metallic cations have an ionic radius of from 1.40 A to the pore size of the specific zeolite. Preferably this will be a combination of TPA and a member selected from the group consisting of TMA, tetraethylammonium (TEA), cesium and rubidium cations. The Dwyer et al U.S. Pat. No. 4,375,458 also indicates that the mixture may also have therein added alkali or alkaline earth metals.

SUMMARY

According to one aspect of the invention, there is provided an improvement in a method of the Dwyer et al U.S. Pat. No. 4,375,458 for making ZSM-5 zeolites from reaction mixture containing TPA and TMA, whereby the uniformity of the crystallite size is increased and the mean crystallite size is further increased. The improvement comprises adding to the aqueous reaction medium a sufficient amount of sodium chloride.

According to another aspect of the invention, there is provided catalyst composition comprising an extrudate of zeolite crystallites and a binder, said crystallites being ZSM-5 crystallites having an average minimum dimension of greater than 3 microns with a size variation of no more than 25 percent in terms of relative standard deviation.

According to another aspect of the present invention, there is provided a process for effecting catalytic conversion of an organic charge which comprises contacting said charge under catalytic conversion conditions with a catalyst comprising a porous crystalline material according to the present invention.

DETAILED DESCRIPTION

The catalysts which are prepared in accordance with the method of the present invention are zeolite based catalysts which promote the conversion of aromatic compounds. One essential component of such catalysts is a particular type of crystalline zeolite material which exhibits unusual properties. Although these zeolites have unusually low alumina contents, i.e. high silica to alumina mole ratios, they are very active even when the silica to alumina mole ratio exceeds 30. Such activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and, therefore, are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra.

The silica to alumina mole ratio of a zeolite may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 70 and above or even 1600 and above. In addition, zeolites as otherwise characterized herein but which are substantially free of aluminum, that is zeolites having silica to alumina mole ratios of up to infinity, are found to be useful and even preferable in some instances.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class herein have an effective pore size such as to freely sorb normal hexane. In addition, their structure provides constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded. Windows of 10-membered rings are usually effective, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Constraint Index (CI) values for some typical materials are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 1.5 |
| H-Zeolon (mordenite) | 0.4 |
| REY | 0.4 |
| Amorphous Silica-Alumina | 0.6 |
| Erionite | 38 |

The above-described Constraint Index is one means of characterizing particular zeolites. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of, e.g., 1 to 12 for the Constraint Index of a particular zeolite. Such a zeolite is to be regarded as having a Constraint Index in the range of 1 to 12. Also contemplated herein as having a Constraint Index in the range of 1 to 12 are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12.

ZSM-5 is described in greater detail in U.S. Pat. No. 3,702,886 and U.S. Pat. No. Re. 29,948. The entire descriptions contained within those patents, particularly the X-ray diffraction pattern of therein disclosed ZSM-5, are incorporated herein by reference.

ZSM-5 zeolites, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air, e.g., from about 15 minutes to about 24 hours. The presence of organic cations in the forming solution may not be absolutely essential to the formation of this type zeolite; however, the presence of these cations does appear to favor the formation of this special class of zeolite. When synthesized in the alkali metal form, a zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used as precursors to the catalysts of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In practicing aromatics conversion processes using the catalysts prepared by the synthesis method of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites as prepared herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The ZSM-5 crystallites of the present invention have been observed to be extremely fracture resistant. Therefore, when extrudates of these crystallites with binders are formed, essentially all of the crystallites may remain unfractured. Even under large grinding forces encountered in severe extruding conditions, the number of fractured crystallites in the extrudate may be less than, e.g., 10 percent.

A second optional component of the aromatics conversion catalysts prepared in accordance with the present invention comprises a minor proportion, e.g., from about 0.05% to 50% by weight of the catalyst composite, of a difficultly reducible oxide. Oxides of this type can include oxides of phosphorus as well as those oxides of the metals of Groups IA, IIA, IIIA, IVA, VA, VIA, VIIA, VIIIA, IB, IIB, IIIB, IVB, or VB of the Periodic Chart of the Elements (Fisher Scientic Company, Catalog No. 5-702-10) which serve to enhance the para-selectivity properties of the catalysts modified therewith. The difficultly reducible oxides most commonly employed to modify the selectivity properties of the zeolite-based catalysts herein are oxides of phosphorus and magnesium. Thus, the catalysts prepared herein can be treated with phosphorus and/or magnesium compounds in the manner described in U.S. Pat. Nos. 3,894,104; 4,049,573; 4,086,287; and 4,128,592, the disclosures of which are incorporated herein by reference.

Phosphorus, for example, can be incorporated into such catalysts at least in part in the form of phosphorus oxide in an amount of from about 0.25% to about 25% by weight of the catalyst composition, preferably from about 0.7% to about 15% by weight. Such incorporation can be readily effected by contacting the zeolite composite with a solution of an appropriate phosphorus compound, followed by drying and calcining to convert phosphorus in the zeolite to its oxide form. Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3–5 hours but may be extended to 24 hours or longer.

Magnesium oxide is another preferred difficultly reducible oxide which can be incorporated with the zeolite composites in a manner similar to that employed with phosphorus. Magnesium can comprise from about 0.25% to 25% by weight preferably from about 1% to 15% by weight present at least in part as magnesium oxide. As with phosphorus, magnesium oxide incorporation is effected by contacting the zeolite composite with an appropriate magnesium compound followed by drying and calcining to convert magnesium in the zeolite to its oxide form. Preferred magnesium-containing compounds include magnesium nitrate and magnesium acetate. Calcination times and temperatures are generally the same as recited hereinbefore for calcination of phosphorus-containing catalysts.

In addition to treatment of the zeolite composites to incorporate phosphorus and/or magnesium oxides as hereinbefore described in detail, such zeolites may also be modified in a substantially similar manner to incorporate thereon a variety of other oxide materials to enhance para-selectivity. Such oxide materials include oxides of boron (U.S. Pat. No. 4,067,920); antimony (U.S. Pat. No. 3,979,472); beryllium (U.S. Pat. No. 4,260,843); Group VIIA metals (U.S. Pat. No. 4,275,256); alkaline earth metals (U.S. Pat. No. 4,288,647); Group IB metals (U.S. Pat. No. 4,276,438); Group IVB metals (U.S. Pat. No. 4,278,827); Group VIA metals (U.S. Pat. No. 4,259,537); Group IA elements (U.S. Pat. No. 4,329,533); cadmium (U.S. Pat. No. 4,384,155); iron and/or cobalt (U.S. Pat. No. 4,380,685); Group IIIB metals (U.S. Pat. No. 4,276,437); Group IVA metals (U.S. Pat. No. 4,302,620); Group VA metals (U.S. Pat. No. 4,302,621); and Group IIIA elements (U.S. Pat. No. 4,302,622).

In addition to the above-described modifications of ZSM-5 by ion exchange or by impregnation with various oxides, the hydrogen form of ZSM-5 (i.e. HZSM-5) may be modified by steaming or by high temperature calcination at temperatures over 1200° F. (i.e., 649° C.). With regard to high temperature calcination European Patent Specification No. 0014545, which claims priority to U.S. application Ser. No. 007,871, filed Jan. 31, 1979, the entire disclosures of which are expressly incorporated herein by reference, teaches that such high temperature calcination increases the ability of ZSM-5 to selectively produce certain para-dialkylaromatic isomers. Note Examples 3 and 4 of these disclosures.

Typical conditions for preparing the zeolite of the present invention include heating an appropriate crystallization mixture at a temperature of from about 80° C. to about 200° C. for a period of time from, e.g., about 4 hours to about 30 days. The digestion of the gel particles is carried out until the crystalline zeolite forms completely. The product crystals are then separated, as by cooling and filtering, and are water washed and dried at from about 80° C. to about 150° C.

The crystallization mixture may have an NaCl to $SiO_2$ molar ratio of, e.g., from 0.1 to 0.4.

Zeolites prepared in accordance with the synthesis aspect of the present invention are useful as catalyst components for a variety of organic, e.g., hydrocarbon, compound conversion processes. Such conversion processes include, as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure of from about atmospheric to about 60 atmospheres and a weight hourly space velocity of from about 0.08 to about 20; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

Typical of the processes contemplated herein are disproportionation of toluene to benzene and xylene, wherein the proportion of para-xylene obtained is greatly in excess of its normal equilibrium concentration. Such process is effectively carried out at a temperature of between about 400° C. and about 700° C. at a pressure between about 1 atmosphere and about 100 atmospheres utilizing a weight hourly space velocity of between about 1 and about 50.

Another charge stock suitable for use in the process of the invention is a stream high in $C_2$–$C_{15}$ olefin content. Thus, ethylene, propylene, butenes, pentenes, hexenes, cycloolefins such as cyclopentene and cyclohexene, alkyl-substituted cycloolefins such ethyl cyclopentene, cyclopentadiene and cyclohexadiene can be effectively converted to a high yield of para dialkyl substituted benzenes utilizing the hereinabove described catalyst. Conversion utilizing such olefin feed is carried out at a temperature within the approximate range of 300° to 700° C., a pressure between atmospheric and 100 atmospheres employing a weight hourly space velocity between about 1 and about 1000. As source of the olefin reactant either substantially pure streams of the $C_2$–$C_{15}$ olefin may be employed or refinery or chemical streams high in such reactant, i.e., generally more than 25 volume percent may be used.

A still further charge stock which can be used effectively with the catalysts of the present invention to selectively produce paradialkyl substituted benzenes containing alkyl groups of 1 to 4 carbon atoms includes paraffinic hydrocarbons having between 3 and 45 carbon atoms. Representative of such paraffins are butanes, pentanes, hexanes, heptanes, octanes, dodecanes, eiconsane, dotriacontane, tetracontane, and alkyl-substituted derivatives of these paraffins. Utilizing such paraffinic charge, reaction conditions include contact with the large crystal size crystalline aluminosilicate zeolite catalyst at a temperature of between about 400° C. to 700° C., a pressure between about atmospheric and about 100 atmospheres and a weight hourly space velocity between about 0.1 and about 100.

The use of mixed aromatics as feed is also feasible. For example, a mixture of ethylbenzene and toluene is converted selectively to a mixture rich in p-diethylbenzene and p-ethyltoluene, the latter predominating at high toluene to ethylbenzene ratios in the feed.

Reaction of benzene, toluene, ethylbenzene, propylbenzene or butylbenzene with $C_2$–$C_{20}$ olefins or $C_5$–$C_{25}$ paraffins at 250° to 500° C. yields p-dialkyl benzenes. This reaction is preferably carried out under pressure greater than 200 psig.

For example, benzene and ethylene at a mole ratio of 1:2 to 10:1 yield p-diethylbenzene besides ethylbenzene (p=400 psig, Temp.=800° F.).

In the absence of added aromatics, $C_2$–$C_{15}$ olefins and $C_3$–$C_{44}$ paraffins each yield a mixture of aromatics rich in p-dialkylbenzenes. The olefins and the higher paraffins are more reactive and require lower severity of operation, e.g., a temperature of 250°–600° C., and preferably 300° C.–550° C., while the lower paraffins, e.g., $C_3$–$C_5$ paraffins yield aromatics at a practical rate only above 400° C. The aromatization can be carried out at atmospheric pressure or at elevated pressure; low pressure hydrogen can be used to retard catalyst aging, but high hydrogen partial pressure about 200 psig diminishes aromatics formation. Production of p-dialkylated benzenes containing alkyl groups greater than $C_1$ is favored by higher pressure and lower temperature. For example, p-ethyltoluene is formed from either dodecane or 1-butene at 400° C., whereas p-xylene is the preferred dialkylbenzene formed at higher temperature.

The unmodified HZSM-5 forms of the zeolites of the present invention are capable of selectively producing large portions of para-isomers of xylene and ethyltoluene under appropriate reaction conditions. More particularly, for example, the para-ethyltoluene content may be from 95 to 99 percent of the ethyltoluene produced when toluene is alkylated with ethylene over these unmodified HZSM-5 zeolites, the para-xylene content may be from 90 to 95 percent of the xylene produced when toluene is disproportionated over these unmodified HZSM-5 zeolites, and the para-xylene content may be from 60 to 77 percent of the xylene produced when toluene is alkylated with methanol over these unmodified HZSM-5 zeolites.

For the purposes of the present specification and claims which follow, unmodified HZSM-5 shall be defined herein as HZSM-5 which has not been subjected to any of the following treatments:
(i) steaming;
(ii) calcination at a temperature of greater than 600° C.; and
(iii) incorporation thereon with an oxide material to enhance the para-selectivity of the HZSM-5.

Unmodified HZSM-5 may be composited with binder materials.

EXAMPLE 1

A silicate solution was prepared by mixing 28.9 parts by weight of Q-brand sodium silicate, (28.5% $SiO_2$, 8.9% $Na_2O$), 16.7 parts by weight $H_2O$, and 0.082 Daxad 27. Daxad 27 is a dispersant which is a sodium salt of polymerized substituted benzoid alkyl sulfonic acid combined with an inert inorganic suspending agent available from W. R. Grace; Polymers and Chemicals Division; Cambridge, Mass. 02140. The solution exhibited a specific gravity of 1.232 at 60° F. An acid alum solution was prepared by mixing 1.0 part by weight of $Al_2(SO_4)_3 \cdot XH_2O$ (16.4% $Al_2O_3$), 2.9 parts by weight of 100 percent $H_2SO_4$, 2.9 parts by weight of an aqueous 50% tetra-methyl-ammonium chloride (TMACl) solution, 8.9 parts by weight of $H_2O$, and 11.5 parts by weight of an aqueous tetra-propyl-ammonium bromide (TPABr) solution obtained by prereacting a mixture of equivalent molar amounts of tri-n-propylamine and n-propylbromide (the nitrogen content of the prereacted organic mixture was 1.5 percent by weight). In the following Examples, the TPABr solution will be referred to as "prereacted organics". The specific gravity of the acid alum solution was 1.110 at 60° F. The above solutions were charged into an autoclave containing 2.2 parts by weight $H_2O$. The charging was performed by feeding the solutions through a mixing nozzle simultaneously. 5.4 parts by weight $H_2O$ were then added to the gel. After whipping the gel at 250 rpm for one hour, 1.9 parts by weight $NaCl$ were added ($NaCl/Al_2O_3$ mole ratio=19). Whipping at 250 rpm was continued for several more hours. The pH of the mixture was observed to drift upward over time. This pH was adjusted to essentially its original level by incremental addition of acid. The mixture was then heated to 320° F. with 40 rpm agitation. Crystallization was complete within 20 hr. The product ZSM-5 exhibited a crystallinity of 125% and a $SiO_2$ to $Al_2O_3$ ratio of 77. Scanning electron micrographs showed a very uniform crystallite size of 15×7×3.5 microns.

EXAMPLE 1a

The preparation of Example 1 was repeated. The silicate solution exhibited a specific gravity at 60° F. of 1.230 and the acid alum, a specific gravity of 60° F. at 1.112. Crystallization was complete in 21.5 hr. The product ZSM-5 had a crystallinity of 125% and a $SiO_2$ to $Al_2O_3$ mole ratio of 76. Scanning electron micrographs showed a very uniform crystallite size of 16×8×4m.

COMPARATIVE EXAMPLE A

A catalyst was prepared in accordance with the procedure of Example 8 of the Dwyer et al U.S. Pat. No. 4,375,458 as follows:

A silicate solution was made by mixing 28.9 parts by weight of Q-brand sodium silicate, 14.2 parts by weight of $H_2O$ and 0.084 part by weight Daxad 27. An acid alum solution was prepared by mixing 1.0 part by weight $Al_2(SO_4)_3 \cdot xH_2O$ (17.2% $Al_2O_3$), 2.4 parts by weight 100% $H_2SO_4$, 2.9 parts by weight 50% TMACl, and 25.1 parts by weight prereacted organics (1.58% N by weight). The calculated TPA to TMA mole ratio was 2.1. The above solutions were charged to an autoclave containing 0.83 parts by weight water. The charging was done by feeding the solutions through a mixing nozzle simultaneously. The final mixture had a calculated % solids of 11%. The gel was whipped for one hour at 90 rpm and at room temperature. The crystallization conditions were 320° F. with 90 rpm agitation. Crystallization was complete within 21 hr. The washed and dried product was found to be 90% ZSM-5 and had a $SiO_2$ to $Al_2O_3$ mole ratio of 74.1. The crystal size was shown by SEM to be in the range 20×12×5 m to 4×3×2 m.

Examples 6 to 8 of U.S. Pat. No. 4,375,458 showed that the maximum crystal size increased from 4×3×2 to 20×12×5 m as the molar ratio of TPA to TMA increased from 0.41 to 2.1.

COMPARATIVE EXAMPLE B

The larger size crystals were separated from the final washed and dried product of Comparative Example A by a series of settling/decantation separations. The size range of the separated large crystal fraction was shown by SEM to be AS-180-6.

COMPARATIVE EXAMPLE C

A catalyst was prepared in accordance to Example 1 but without the addition of $NaCl$ as follows:

A silicate solution was made by mixing 28.9 parts by weight of Q-brand sodium silicate, 16.7 parts by weight of $H_2O$, and 0.082 part of Daxad 27. An acid alum solution was made by mixing 1.0 part by weight of $Al_2(SO_4)_3 \cdot xH_2O$, 2.7 parts by weight of 100% $H_2SO_4$, 2.9 parts by weight of 50% TMACl, 11.7 parts by weight of prereacted organics, and 15.5 parts by weight of $H_2O$. The solutions were charged to an autoclave and gel whipped at 90 rpm for 2 hr. The calculated % solids of the final mixture was 11%. Crystallization was carried out at 320° F. and 60 rpm agitation. The washed and dried product ZSM-5 had a crystallinity of 125% and a $SiO_2$ to $Al_2O_3$ mole ratio of 68.0. The crystal size was shown by SEM to be $3 \times 1 \times 0.6$ m.

COMPARATIVE EXAMPLE D

The preparation of Comparative Example C was repeated. The washed and dried product ZSM-5 had a $SiO_2$ to $Al_2O_3$ mole ratio of 74.3 and a crystallinity of 130%. The crystal size was shown to be $6 \times 4 \times 1.5$ m.

EXAMPLE 2

In order to demonstrate the more intrinsic para selectivity of the uniformly large ZSM-5 crystallites of Examples 1 and 1a, the diffusion rates of ortho-xylene through the Example 1 and 1a catalysts and the Comparative Examples A-D catalysts were examined. The catalysts were prepared for the ortho-xylene sorption test according to the following procedure: (1) calcination in $N_2$ for three hours at 1000° F.; (2) two ammonium exchanges at room temperature with 1N $NH_4NO_3$; and (3) calcination for 3 hr at 1000° F. in air. Sorption rates were measured at 250° F. with an ortho xylene partial pressure of 0.010. Values of the sorption parameter $D/l^2$, where D is the diffusivity of ortho xylene and l is the length of the diffusion path, are shown in Table 1 for the crystallites of the previous Examples. These data demonstrate that the uniformly large crystallites of the Examples 1 and 1a preparations and those obtained by settling/decantation separation exhibit substantially lower values of $D/l^2$ than the crystallites of Comparative Examples A, C and D. This is because the diffusion path is longer in the larger crystallites. In particular, for the Examples 1 and 1a preparations, the values of $D/l^2$ are from six to 200 times lower than those of Comparative Examples A, C, and D. Intrinsic para selectivity is enhanced for crystallites which exhibit slower rates of o-xylene diffusion, i.e., lower values of $D/l^2$

TABLE 1

| Ortho-Xylene Diffusion Parameters for Large Crystal ZSM-5 | |
|---|---|
| Preparation | $D/l^2$ ($sec^{-1}$) $\times 10^6$ |
| Example 1 | 0.21 |
| Example 1a | 0.14 |
| Comparative Example B | 0.29 |
| Comparative Example A | 0.9 |
| Comparative Example C | 28 |
| Comparative Example D | 2.2 |

EXAMPLE 3

The catalytic activity in the alkylation of toluene with ethylene was compared for the Comparative Example D catalyst and the Example 1 catalyst as a function of magnesium loading. Finished catalysts were prepared from the crystallites in the following way: (1) extrusion into 65% ZSM-5/35% $Al_2O_3$ 1/16-inch cylinders; (2) calcination for three hours at 1000° F. in nitrogen; (3) two ammonium exchanges with 1N $NH_4NO_3$ at room temperature followed by drying at 250° F.; (4) impregnation with an aqueous $Mg(NO_3)_2$ solution followed by drying at 250° F.; (5) air calcination for three hours at 1000° F.; and (6) subsequent magnesium impregnation and calcination as necessary to achieve the desired magnesium loading. The catalyst of Example 1 required less than half the magnesium loading of the Comparative Example D catalyst to achieve para-ethyltoluene selectivities of greater than 96% and ethylene conversions of comparable magnitude at equivalent process conditions. The results are summarized in Table 2.

TABLE 2

| Catalytic Performance as a Function of Mg Loading 810° F., 100 psig, 29/1/0.25 Toluene/Ethylene/$H_2$ WHSV | | | |
|---|---|---|---|
| Preparation | % Mg | % PET/ET[1] | % Ethylene Conversion |
| Comparative Ex. D | 6.7 | 98.9 | 78.1 |
| | 5.3 | 59.9 | 83.2 |
| Example 1 | 7.7 | 99.1 | 5.9 |
| | 3.9 | 98.0 | 73.9 |
| | 2.8 | 96.9 | 74.5 |

[1]Para-ethyltoluene (PET) selectivity reported as percent PET of the ethyltoluene (ET) isomers.

EXAMPLE 4

The ZSM-5 crystallites of Example 1a were calcined in nitrogen at 1000° F. followed by ammonium exchange and final air calcination at 10000° F. to obtain the hydrogen form of the ZSM-5. Toluene was alkylated with ethylene over the HZSM-5 crystallites of Example 1a to give a high percentage of para isomer in the ethyltoluene product. The results are summarized in Table 3.

TABLE 3

| Alkylation of Toluene with Ethylene to Produce Para-ethyltoluene Pressure = 1 atm TOL/$C_2H_4$ Feed: | | | | |
|---|---|---|---|---|
| Temp., °C. | Total WHSV | Mole Ratio | TOL Conv, %[a] | PET/ET, %[b] |
| 300 | 14.8 | 4.38 | 2.5 | 90.8 |
| 325 | 14.8 | 4.38 | 3.8 | 95.8 |
| 350 | 14.8 | 4.38 | 7.1 | 95.1 |
| 300 | 14.3 | 8.75 | 6.8 | 93.9 |
| 325 | 14.3 | 8.75 | 37.7 | 95.1 |
| 350 | 14.3 | 8.75 | 59.0 | 92.6 |
| 350 | 28.5 | 17.4 | 66.5 | 98.8 |
| 375 | 28.5 | 17.4 | 70.8 | 98.5 |
| 375 | 28.5 | 17.4 | 59.5 | 98.5 |
| 375 | 28.5 | 17.4 | 61.4 | 98.5 |

[a]Calculated as % of theoretical.
[b]p-ethyltoluene/total ethyltoluenes, %

Toluene was disproportionated over the hydrogen-form ZSM-5 crystallites of Example 1a to give xylene and benzene having a high percentage of para isomer in the xylene product. The results are summarized in Table 4.

TABLE 4

| Selective Toluene Disproportionation Pressure = 1 atm | | | |
|---|---|---|---|
| Temp., °C. | WHSV, $hr^{-1}$ | TOL conv, % | PX/XYL, % |
| 400 | 14.0 | 1.4 | 95.1 |
| 450 | 14.0 | 3.2 | 94.0 |
| 500 | 14.0 | 5.4 | 93.4 |
| 550 | 14.0 | 6.6 | 92.4 |
| 600 | 14.0 | 5.3 | 90.2 |

EXAMPLE 6

Toluene was alkylated with methanol over a catalyst containing unmodified HZSM-5 crystallites prepared in accordance with Example 1a to produce p-xylene and water. Results under a variety of temperatures and space velocities are summarized in Tables 5 and 6.

TABLE 5

Alkylation of Toluene with Methanol to Produce P—Xylene[a]

| Temp. °C. | TOL/MeOH WHSV | TOL/MeOH Mole Ratio | Conv. % TOL | Conv. % MeOH | Selectivity, wt % Xylenes | Selectivity, wt % Benzene | Selectivity, wt % ET | Selectivity, wt % Oth. Ar.[c] | Xylene, % Para | Xylene, % Meta | Xylene, % Ortho | PET[b] ET |
|---|---|---|---|---|---|---|---|---|---|---|---|---|
| 400 | 2.09 | 4/1 | 11.2 | 99 | 55.2 | 14.3 | 10.6 | 4.1 | 65.0 | 27.2 | 7.8 | 75.9 |
| 425 | — | — | 10.9 | 96 | 63.6 | 15.3 | 6.8 | 3.6 | 61.7 | 29.4 | 8.9 | 73.6 |
| 450 | — | — | 11.7 | 94 | 63.9 | 14.4 | 4.3 | 3.4 | 60.6 | 30.3 | 9.1 | 71.2 |
| 475 | — | — | 10.9 | 94 | 66.8 | 15.5 | 3.1 | 3.4 | 59.6 | 30.9 | 9.5 | 64.9 |
| 425 | 4.1 | 4/1 | 9.6 | 95.8 | 58.34 | 13.9 | 10.5 | 4.5 | 71.3 | 22.5 | 6.2 | 83.9 |
| 450 | — | — | 7.8 | 85.5 | 64.9 | 12.5 | 5.6 | 3.4 | 68.6 | 24.3 | 7.1 | 77.3 |
| 475 | — | — | 6.3 | 81 | 66.9 | 13.2 | 3.2 | 3.1 | 66.7 | 25.5 | 7.8 | 74.1 |
| 475 | — | — | 5.2 | 77 | 69.7 | 14.3 | 2.0 | 3.5 | 65.1 | 26.3 | 8.6 | 71.0 |

[a]atmospheric pressure
[b]percent p-ethyltoluene in total ethyltoluene by-product
[c]balance of products are gases

TABLE 6

Alkylation of Toluene with Methanol to Produce P—Xylene[a]

| Temp. °C. | TOL/MeOH WHSV | TOL/MeOH Mole Ratio | Conv. % TOL | Conv. % MeOH | Selectivity, wt % Xylenes | Selectivity, wt % Benzene | Selectivity, wt % ET | Selectivity, wt % Oth. Ar.[c] | Xylene, % Para | Xylene, % Meta | Xylene, % Ortho | PET[b] ET |
|---|---|---|---|---|---|---|---|---|---|---|---|---|
| 450 | 10.0 | 4/1 | 6.9 | 91 | 62.8 | 8.6 | 10.7 | 3.6 | 74.5 | 20.3 | 5.2 | 81.3 |
| 500 | — | — | 5.8 | 77.5 | 70.4 | 11.5 | 3.4 | 2.8 | 68.0 | 25.2 | 6.8 | 71.2 |
| 550 | — | — | 5.5 | 69.5 | 67.3 | 16.9 | 1.3 | 2.2 | 66.0 | 26.1 | 7.9 | 67.6 |
| 600 | — | — | 1.9 | 66 | 60.8 | 21.0 | .4 | 3.2 | 69.1 | 21.8 | 9.1 | 85.5 |
| 450 | 20.0 | 4/1 | 2.7 | 68.8 | 60.0 | 12.3 | 6.7 | 4.6 | 76.9 | 18.4 | 4.7 | 80.6 |
| 500 | — | — | 0.7 | 65.3 | 65.2 | 10.3 | 2.2 | 1.2 | 71.2 | 22.5 | 6.3 | 73.4 |
| 550 | — | — | .3 | 66.3 | 56.3 | 22.5 | .9 | 2.6 | 69.7 | 23.0 | 7.3 | 71.2 |
| 600 | — | — | .2 | 61.0 | 58.2 | 25.8 | .4 | 2.7 | 70.4 | 20.9 | 8.7 | 100 |

[a]atmospheric pressure
[b]percent p-ethyltoluene in total ethyltoluene by-product
[c]balance of products are gases Atmospheric pressure and a constant toluene/methanol molar feed ratio of 4/1 was used. It can be seen that the para isomer in the xylene product varied from about 60–77%. Toluene disproportionation, as indicated by the presence of benzene also contributed to the xylene product. In general, xylene selectivity increased with increases in temperature, while the proportion of para isomer decreased.

What is claimed is:

1. A catalyst composition comprising an extrudate of zeolite crystallites and a binder, said crystallites being ZSM-5 crystallites having an average minimum dimension of greater than 3 microns with a size variation of no more than 25 percent in terms of relative standard deviation.

2. A catalyst composition according to claim 1, wherein said binder is clay.

3. A catalyst composition according to claim 1, wherein said binder is selected from the group consisting of alumina, silica, silica-alumina, silica-magnesia, silica-zirconia, silica-thoria, silica-beryllia, silica-titania, silica-alumina-thoria, silica-alumina-zirconia, silica-alumina-magnesia and silica-magnesia-zirconia.

4. A catalyst composition according to claim 1, wherein said ZSM-5 crystallites comprise from about 1 to about 99 percent by weight of the total crystallites plus binder.

5. A catalyst composition according to claim 1, wherein said ZSM-5 crystallites comprise from about 5 to about 80 percent by weight of the total crystallites plus binder.

6. A catalyst composition according to claim 5, wherein said binder is alumina.

7. A catalyst composition according to claim 6, wherein said crystallites have an average crystallite size of 16×8×4 microns.